(12) United States Patent
Sanpei et al.

(10) Patent No.: US 8,034,931 B2
(45) Date of Patent: Oct. 11, 2011

(54) PROCESS FOR PRODUCING SUBSTITUTED AMINOQUINAZOLINONE DERIVATIVE, INTERMEDIATE THEREFOR, AND PEST CONTROL AGENT

(75) Inventors: Osamu Sanpei, Kawachinagano (JP); Masahiro Uehara, Kawachinagano (JP); Nobuyuki Niino, Kawachinagano (JP); Hiroki Kodama, Kawachinagano (JP); Kazuyuki Sakata, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 1169 days.

(21) Appl. No.: 10/556,218

(22) PCT Filed: May 11, 2004

(86) PCT No.: PCT/JP2004/006256
§ 371 (c)(1),
(2), (4) Date: Nov. 10, 2005

(87) PCT Pub. No.: WO2004/099184
PCT Pub. Date: Nov. 18, 2004

(65) Prior Publication Data
US 2007/0185142 A1    Aug. 9, 2007

(30) Foreign Application Priority Data

May 12, 2003 (JP) ................. 2003-133332
Jun. 18, 2003 (JP) ................. 2003-173333

(51) Int. Cl.
*C07D 239/80* (2006.01)
(52) U.S. Cl. ...................................... 544/316
(58) Field of Classification Search ............ 544/316
See application file for complete search history.

(56) References Cited

FOREIGN PATENT DOCUMENTS

| JP | 60-81156 | 5/1985 |
|---|---|---|
| JP | 8-325239 | 12/1996 |
| JP | 10-204084 | 8/1998 |
| JP | 11-158180 | 6/1999 |
| JP | 2001-64107 | 3/2001 |
| JP | 2001-342186 | 12/2001 |
| JP | 2002-255933 | 9/2002 |
| JP | 2003-104985 | 4/2003 |

OTHER PUBLICATIONS

Grubbs et al. New Approaches to Olefin Cross-Metathesis, 2000, Journal of the American Chemical Society, 122, 58-71.*

Kornet, M.J. et al., Synthesis of 3-Amino-3, 4-dihydro-2(1H)-quinazolinones as Potential Anticonvulsants, J. Heterocycl. Chem., 1984, 21, pp. 1709-1711.

* cited by examiner

*Primary Examiner* — James O Wilson
*Assistant Examiner* — Brian McDowell
(74) *Attorney, Agent, or Firm* — Paul E. White, Jr.; Manelli Selter PLLC

(57) ABSTRACT

A process for producing a substituted aminoquinazolinone derivative of formula (I), characterized by reducing a substituted iminoquinazolinone derivative of formula (II) with hydrogen in the presence of a catalyst and either of a halogen compound and a sulfur compound; a substituted iminoquinazolinone derivative of formula (II'); and a pest control agent containing the derivative of formula (II') or a salt thereof as an active ingredient and a method of using the same (in the formulae, R represents hydrogen, formyl, $(C_1$-$C_6)$ alkyl, $(C_1$-$C_6)$alkoxy$(C_1$-$C_3)$alkyl, $(C_1$-$C_6)$ alkylsulfonyl, optionally substituted phenylcarbonyl, etc.; $R^1$ represents an optionally substituted, 5- or 6-membered heterocycle having one to three heteroatoms selected among oxygen, sulfur, and nitrogen; $R^2$ represents hydrogen or $(C_1$-$C_3)$ alkyl; X and X' may be the same or different and each represents $(C_1$-$C_6)$ haloalkyl, $(C_1$-$C_6)$ haloalkoxy, etc.; n is an integer of 0; and n' is an integer of 1-4).

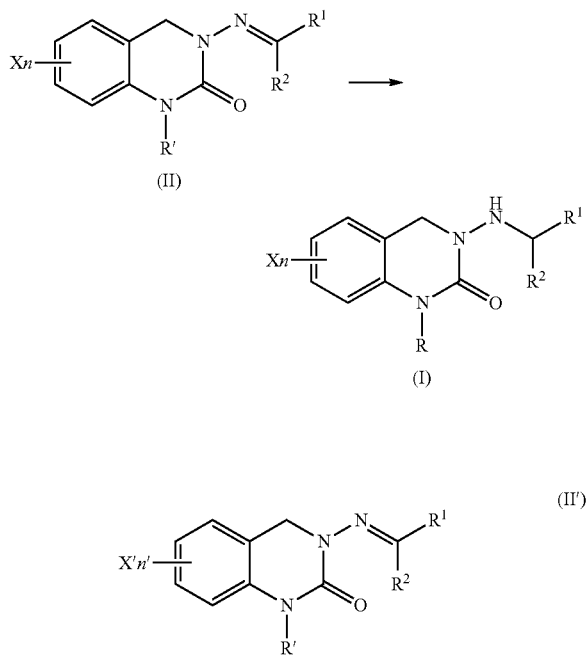

3 Claims, No Drawings

PROCESS FOR PRODUCING SUBSTITUTED AMINOQUINAZOLINONE DERIVATIVE, INTERMEDIATE THEREFOR, AND PEST CONTROL AGENT

This application is the national phase of international application PCT/JP2004/006256 filed 11 May 2004 which designated the U.S.

TECHNICAL FIELD

The present invention relates to a process for producing a substituted aminoquinazolinone derivative useful as a pest control agent. In addition, the present invention relates to intermediates and salts of the derivative, a pest control agent containing any of them as an active ingredient, and its usage.

BACKGROUND ART

The substituted aminoquinazolinone derivative described herein is useful as a pest control agent. As a process for producing this derivative, there is known a process of reducing the nitrogen-carbon double bond of a substituted iminoquinazolinone derivative with hydrogen in the presence of a catalyst (see, for example, JP-A-8-325239 and JP-A-2001-342186).

As a general production process in which a hydrazone is converted to a hydrazine by reduction with hydrogen, there are known processes, i.e., a process using a platinum oxide as a catalyst (see, for example, J. Med. Chem., 6, 221 (1963)) and a process using palladium-carbon as a catalyst (see, for example, J. Org. Chem., 26, 1854 (1961)).

These prior art references, however, do not disclose an additive for hydrogen reduction which is characteristic of the present invention.

In addition, it is also known that compounds analogous to a substituted iminoquinazolinone derivative formed as an intermediate in the production process of the present invention are useful as pest control agents (see, for example, JP-A-8-325239 and JP-A-2001-342186).

DISCLOSURE OF INVENTION

Problem to be Solved by the Invention

For the production of a substituted amino-quinazolinone derivative, the processes disclosed in the above prior art references have been disadvantageous in that since by-products are produced by hydrogenolysis, both the selectivity and yield of the desired compound are insufficient. Therefore, there has been a desire for a process that solves this problem and permits industrially efficient production of a substituted aminoquinazolinone derivative.

Heretofore known substituted iminoquinazolinone derivatives are not always satisfactory in performance characteristics as pest control agents from the viewpoint of practical dosage, insecticidal spectrum, residual effect and the like. Accordingly, there has been a desire for the development of a more excellent pest control agent.

Means for Solving the Problem

The present inventors earnestly investigated in order to solve the above problem, and consequently found that the addition of a halogen-containing compound or a sulfur-containing compound as an additive in the reduction with hydrogen using a catalyst markedly improves the selectivity and the yield as compared with conventional processes. Further, they also found that some of intermediates formed in the production of an aminoquinazolinone are novel compounds, have equal or more effect even at a low dosage as compared with heretofore known substituted iminoquinazolinone derivatives, and have an excellent controlling effect on whiteflies, scales and the like, which are injurious to agriculture and horticulture. On the basis of this finding, the present invention has been accomplished.

That is, the present invention relates to a process for producing a substituted aminoquinazolinone derivative represented by general formula (I):

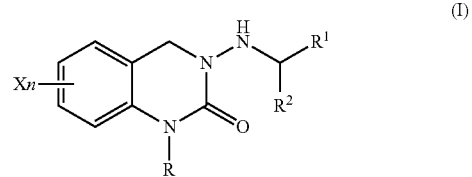

(wherein R, $R^1$, $R^2$, X and n are as defined below), which comprises reducing a substituted iminoquinazolinone derivative represented by general formula (II):

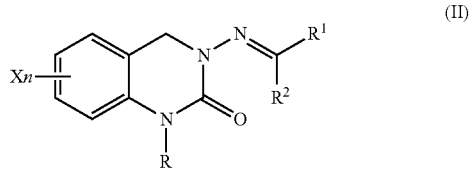

(wherein R is a hydrogen atom; a formyl group; a ($C_1$-$C_6$) alkyl group; a ($C_1$-$C_6$)alkoxy($C_1$-$C_3$)alkyl group; a ($C_1$-$C_6$) alkylsulfonyl group; a cyano($C_1$-$C_3$)alkyl group; a ($C_1$-$C_6$) alkylcarbonyl group; a ($C_1$-$C_6$)alkoxycarbonyl group; a ($C_1$-$C_3$)alkoxy($C_1$-$C_6$)alkylcarbonyl group; a ($C_3$-$C_6$) cycloalkylcarbonyl group; a phenylcarbonyl group; a substituted phenylcarbonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$)alkoxy group, a halo($C_1$-$C_6$)alkoxy group, a ($C_1$-$C_6$) alkylthio group, a halo($C_1$-$C_6$)alkylthio group and a phenyl group; a phenylsulfonyl group; a substituted phenylsulfonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$)alkoxy group, a halo($C_1$-$C_6$)alkoxy group, a ($C_1$-$C_6$)alkylthio group and a halo($C_1$-$C_6$)alkylthio group; or a naphthylcarbonyl group, $R^1$ is a 5- or 6-membered heterocyclic group having 1 to 3 heteroatoms which may be the same or different and are selected from the group consisting of oxygen atom, sulfur atom and nitrogen atom, said heterocyclic group being able to have 1 to 5 substituents which may be the same or different and are selected from the group consisting of a halogen atom, a cyano group, a ($C_1$-$C_6$)alkyl group, a halo($C_1$-$C_6$)alkyl group and a ($C_1$-$C_6$)alkoxy group, and a nitrogen atom in the heterocyclic group being able to represent an N-oxide group, $R^2$ is a hydrogen atom or a ($C_1$-$C_3$)alkyl group, each of Xs, which may be the same or different, is a halogen atom, a ($C_1$-$C_6$)alkyl group, a halo ($C_1$-$C_6$) alkyl group, a ($C_1$-$C_6$) alkoxy group, a halo ($C_1$-$C_6$)alkoxy group or a pentafluorosulfanyl group, and n is an integer of 0 to 4) with hydrogen in the presence of a catalyst and a halogen-containing compound or a sulfur-containing compound.

The present invention relates also to substituted iminoquinazolinone derivatives represented by general formula (II'):

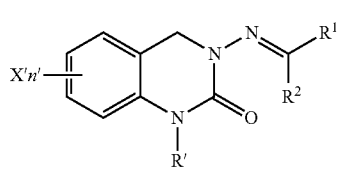

(wherein R' is a formyl group; a ($C_1$-$C_6$)alkyl group; a ($C_1$-$C_6$)alkoxy($C_1$-$C_3$)alkyl group; a ($C_1$-$C_6$)alkylsulfonyl group; a cyano($C_1$-$C_3$)alkyl group; a ($C_1$-$C_6$)alkylcarbonyl group; a ($C_1$-$C_6$)alkoxycarbonyl group; a ($C_1$-$C_3$)alkoxy($C_1$-$C_6$)alkylcarbonyl group; a ($C_3$-$C_6$)cycloalkylcarbonyl group; a phenylcarbonyl group; a substituted phenylcarbonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$)alkoxy group, a halo($C_1$-$C_6$)alkoxy group, a ($C_1$-$C_6$)alkylthio group, a halo($C_1$-$C_6$)alkylthio group and a phenyl group; a phenylsulfonyl group; a substituted phenylsulfonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$) alkoxy group, a halo($C_1$-$C_6$)alkoxy group, a ($C_1$-$C_6$)alkylthio group and a halo($C_1$-$C_6$)alkylthio group; or a naphthylcarbonyl group, $R^1$ is a 5- or 6-membered heterocyclic group having 1 to 3 heteroatoms which may be the same or different and are selected from the group consisting of oxygen atom, sulfur atom and nitrogen atom, said heterocyclic group being able to have 1 to 5 substituents which may be the same or different and are selected from the group consisting of a halogen atom, a cyano group, a ($C_1$-$C_6$)alkyl group, a halo($C_1$-$C_6$)alkyl group and a ($C_1$-$C_6$)alkoxy group, and a nitrogen atom in the heterocyclic group being able to represent an N-oxide group, $R^2$ is a hydrogen atom or a ($C_1$-$C_3$)alkyl group, each of X's, which may be the same or different, is a halo($C_1$-$C_6$)alkyl group, a halo($C_1$-$C_6$)alkoxy group or a pentafluorosulfanyl group, and n' is an integer of 1 to 4) which are some of intermediates in the production of an aminoquinazolinone, or salts thereof, pest control agents containing any of them as an active ingredient, and a method for using the same.

ADVANTAGES OF THE INVENTION

The reduction with hydrogen according to the present invention proceeds very easily with high selectivity. As a result, the yield can be greatly improved as compared with conventional production processes, so that a more advantageous industrial production process of a substituted aminoquinazolinone derivative can be provided.

In addition, the present invention provides a pest control agent having excellent effect even at a low dosage, in particular, excellent controlling effect on whiteflies, scales and the like, which are injurious to agriculture and horticulture, as compared with heretofore known substituted iminoquinazolinone derivatives.

BEST MODE FOR CARRYING OUT THE INVENTION

The present invention is explained below in detail.
1. Definition of the Substituents In the definition of the substituents of the substituted aminoquinazolinone derivative or substituted iminoquinazolinone derivative represented by general formula (I) and general formula (II) or (II'), respectively, the term "halogen atom" means a chlorine atom, a bromine atom, an iodine atom or a fluorine atom. The term "($C_1$-$C_6$)alkyl group" means a linear or branched alkyl group of 1 to 6 carbon atoms, such as methyl group, ethyl group, n-propyl group, i-propyl group, n-butyl group, i-butyl group, s-butyl group, t-butyl group, n-pentyl group, n-hexyl group or the like. The term "halo ($C_1$-$C_6$) alkyl group" means a substituted linear or branched alkyl group of 1 to 6 carbon atoms having as the substituent(s) one or more halogen atoms which may be the same or different, such as trifluoromethyl group, pentafluoroethyl group, 1,2,2,2-tetrafluoro-1-(trifluoromethyl)ethyl group, perfluoropentyl group, perfluorohexyl group or the like. The term "5- or 6-membered heterocyclic group having one or more heteroatoms which may be the same or different and are selected from the group consisting of oxygen atom, sulfur atom and nitrogen atom" means a 5- or 6-membered heterocyclic group such as furan, thiophene, pyrrole, oxazole, thiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pyrrolidine, piperidine, morpholine, thiomorpholine, dithiolan, dithian, piperazine, dioxolane, imidazolidine, tetrahydrofuran or the like.
2. Production of a Substituted Aminoquinazolinone Derivative from a Substituted Iminoquinazolinone Derivative As the catalyst usable in the present invention, there can be exemplified palladium-based catalysts such as palladium-carbon, palladium black, palladium-metal, etc.; nickel-based catalysts such as Raney nickel, nickel-diatomaceous earth, etc.; ruthenium-based catalysts such as ruthenium oxide, ruthenium-carbon, etc.; rhodium-based catalysts such as rhodium chloride, rhodium-carbon, etc.; and platinum-based catalysts such as platinum-carbon, platinum oxide, etc. As to the amount of the catalyst used, the catalyst may be used in the range of 0.0001 to 0.2 mole, preferably 0.001 to 0.1 mole, per mole of the substituted imino-quinazolinone derivative represented by general formula (II).

The additive used in the present invention is a halogen-containing compound or a sulfur-containing compound. The halogen-containing compound includes, for example, molecular halogens such as bromine, iodine, etc.; halogenated hydrocarbons such as methyl iodide, ethyl bromide, 1-iodo-2-methylpropane, iodobenzene, etc.; α-haloketones such as dichloroacetone, 2-iodoacetamide, bromoacetic acid, etc.; N-haloimides such as N-iodosuccinimide, N-bromosuccinimide, 5,5-dimethyl-1,3-diiodohydantoin, etc.; alkali metal halides such as potassium chloride, sodium bromide, sodium iodide, potassium iodide, etc.; alkaline earth metal halides such as magnesium chloride, calcium chloride, magnesium bromide, calcium bromide, strontium bromide, beryllium iodide, magnesium iodide, calcium iodide, barium iodide, etc.; transition metal halides such as nickel chloride, cuprous chloride, cupric chloride, palladium iodide, ferrous chloride, ferric chloride, etc.; and hydrogen halide acids such as hydrochloric acid, hydrobromic acid, hydroiodic acid, etc. The sulfur-containing compound includes, for example, sulfides such as dimethyl sulfide, diphenyl sulfide; etc.; sulfoxides such as dimethyl sulfoxide, diphenyl sulfoxide, etc.; and sulfones such as dimethyl sulfone, diphenyl sulfone, etc. The amount of the additive used may be properly chosen in the range of 0.01 to 1000 moles, preferably 0.1 to 20 moles, per mole of the catalyst.

In the reaction according to the present invention, an acid may be added as a reaction accelerator as known in the case of usual reduction with hydrogen (see, for example, Chemical Society of Japan, "Shin Jikken Kagaku Kouza (New Experimental Chemistry)", Vol. 15, p. 408, 1977, Maruzen Co., Ltd.). As the acid which may be added, there can be exemplified organic carboxylic acids such as formic acid, acetic acid, trifluoroacetic acid, propionic acid, oxalic acid, etc.; organic sulfonic acids such as methanesulfonic acid, trifluoromethanesulfonic acid, p-toluenesulfonic acid, etc.; and inorganic acids such as hydrochloric acid, sulfuric acid, perchloric acid, etc. As to the amount of the acid used, the acid may be used in an amount properly chosen in the range of 0.1 to 100 moles, preferably 0.1 to 10 moles, per mole of the substituted iminoquinazolinone derivative represented by general formula (II).

As a solvent usable in the reaction according to the present invention, any solvent may be used so long as it does not inhibit the progress of the reaction. There may be used, for example, aromatic hydrocarbons such as toluene, xylene, etc.; ethers such as diethyl ether, tetrahydrofuran, dioxane, etc.; halogenated hydrocarbons such as dichloromethane, chloroform, 1,2-dichloroethane, etc.; amide solvents such as dimethylformamide, dimethylacetamide, N-methylpyrrolidone, etc.; alcohol solvents such as methanol, ethanol, etc.; ester solvents such as acetonitrile, dimethyl sulfoxide, ethyl acetate, n-butyl acetate, etc.; acetic acid; and water. These solvents may be used singly or as a mixed solvent thereof.

Although the reaction temperature may be chosen in the range of 0 to 200° C., it is preferably in the range of room temperature to 100° C. Although the reaction time is varied depending on the scale of reaction and the reaction temperature, it may be chosen in the range of 0.5 to 24 hours. The hydrogen pressure may be properly adjusted in the range of 1 to 10 kg/cm$^2$.

The compound represented by general formula (II), an intermediate can be produced according to the process disclosed in JP-A-8-325239 or JP-A-2001-342186 or the process described hereinafter.

3. Substituted Iminoquinazolinone Derivative

The substituted iminoquinazolinone derivative represented by general formula (II') of the present invention is a novel compound not known in any literature. In this compound, R' is preferably a formyl group, a $(C_1\text{-}C_6)$alkyl group, a $(C_1\text{-}C_6)$alkylcarbonyl group, a $(C_1\text{-}C_6)$alkoxycarbonyl group, a phenylcarbonyl group or a substituted phenylcarbonyl group, and is particularly preferably a $(C_1\text{-}C_6)$alkylcarbonyl group; R$^1$ is preferably pyridyl group, in particular, a 3-pyridyl group; R$^2$ is particularly preferably a hydrogen atom; X' is preferably a halo$(C_1\text{-}C_6)$alkyl group or a pentafluorosulfanyl group, and is particularly preferably a 1,2,2,2-tetrafluoro-1-(trifluoromethyl)ethyl group; and n' is preferably an integer of 1 or 2, in particular, 1.

As the salt of the substituted iminoquinazolinone derivative represented by general formula (II') of the present invention, there can be exemplified salts with a mineral acid such as hydrochloric acid, sulfuric acid, nitric acid or the like, as well as salts with an alkali metal atom such as sodium, potassium or the like. The substituted iminoquinazolinone derivative represented by general formula (II') or salt thereof of the present invention has two geometrical isomers due to a carbon-nitrogen double bond in its structural formula in some cases. The present invention includes all of the individual geometrical isomers and mixtures consisting of these isomers in any ratio.

The substituted iminoquinazolinone derivative represented by general formula (II') of the present invention can be produced, for example, by the production process described below and based on the process disclosed in JP-A-8-325239 or JP-A-2001-342186. Production process 1.

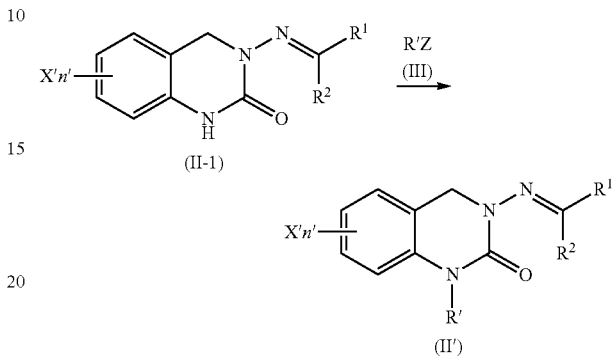

wherein R', R$^1$, R$^2$, X' and n' are as defined above, and Z is a leaving group such as a halogen atom.

The substituted iminoquinazolinone derivative of general formula (II') can be produced by allowing an iminoquinazolinone derivative of general formula (II-1) to react with a compound of general formula (III) in the presence of an inert solvent and a base.

As the inert solvent usable in this reaction, any inert solvent may be used so long as it does not markedly inhibit the progress of the reaction. There can be exemplified inert solvents including, for example, alcohols such as methanol, ethanol, propanol, butanol, etc.; halogenated hydrocarbons such as dichloromethane, chloroform, carbon tetrachloride, etc.; aromatic hydrocarbons such as benzene, toluene, xylene, monochlorobenzene, etc.; nitriles such as acetonitrile, benzonitrile, etc.; Cellosolves such as methyl Cellosolve, etc.; ethers such as diethyl ether, diglyme, dioxane, tetrahydrofuran, etc.; amides such as dimethylformamide, dimethylacetamide, 1-methyl-2-pyrrolidone, etc.; 1,3-dimethyl-2-imidazolidinone; dimethyl sulfoxide; sulfolane; and water. These inert solvents may be used singly or as a mixture thereof.

As the base, inorganic bases or organic bases can be used. There can be exemplified hydroxides such as lithium hydroxide, sodium hydroxide, potassium hydroxide, magnesium hydroxide, etc.; carbonates such as sodium carbonate, sodium hydrogencarbonate, potassium carbonate, etc.; alcoholates such as sodium methoxide, sodium ethoxide, sodium t-butoxide, potassium methoxide, potassium ethoxide, potassium t-butoxide, etc.; alkali metal hydrides such as lithium hydride, sodium hydride, potassium hydride, etc.; alkali metals such as metallic lithium, metallic sodium, metallic potassium, etc.; and organic bases such as triethylamine, pyridine, 1,8-diazabicyclo[5.4.0]undeca-7-ene, etc. As to the amount of the base used, the reaction may be carried out by using the base in an amount properly chosen in the range of 1 mole to excess moles per mole of the iminoquinazolinone derivative of general formula (II-1).

Since the reaction is an equimolar reaction, it is sufficient that the iminoquinazolinone derivative of general formula (II-1) and the compound of general formula (III) are used in equimolar amounts, though either of these reactants may be used in excess. It is preferable to use the compound of general formula (III) in excess.

As to the reaction temperature, the reaction may be properly carried out in the range of −40° C. to the boiling point of the inert solvent used, preferably −10° C. to 60° C. Although the reaction time is varied depending on the scale of reaction, the reaction temperature and the like, it ranges from several minutes to 48 hours.

After completion of the reaction, the desired compound is isolated from the reaction system containing the desired compound by a conventional method, and if necessary, purified by recrystallization, silica gel chromatography, etc., whereby the desired compound can be produced.

The iminoquinazolinone derivative of general formula (II-1) as starting compound can be produced according to the process disclosed in JP-A-8-325239 or JP-A-2001-342186. As the iminoquinazolinone derivative of general formula (II-1), a compound (II-2) in which X' is a 2,2,2-trifluoro-1-(trifluoromethyl)ethyl group and its substitution position is the 6-position in the quinazoline ring can be produced from the aniline derivative (IV) disclosed in JP-A-2003-34673 according to the process disclosed in JP-A-8-325239 or JP-A-2001-342186, as schematically shown below:

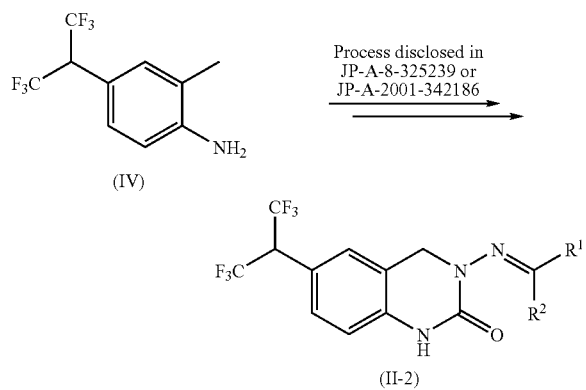

As the iminoquinazolinone derivative of general formula (II-1), a compound (II-3) in which X' is a pentafluorosulfanyl group and its substitution position is the 6-position in the quinazoline ring can be produced from the aniline derivative (IV') disclosed in a published reference (see, for example, JP-A-2004-26815) according to the process disclosed in JP-A-8-325239 or JP-A-2001-342186, as schematically shown below:

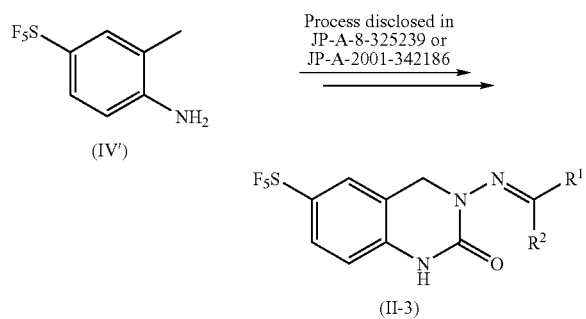

4. Pest Control Agent and its Usage

The pest control agent, containing the substituted iminoquinazolinone derivative represented by general formula (II') or salt thereof of the present invention as an active ingredient, is suitable for controlling various insect pests such as agro-horticultural insect pests, stored grain insect pests, sanitary insect pests, nematodes, etc., which are injurious to paddy rice, vegetables, fruit trees, other crops, flowers, ornamental plants, etc. It has insecticidal effect also on, for example, HEMIPTERA including tea green leafhopper (*Empoasca brassicae*), green rice leafhopper (*Nephotettix cincticepts*), brown rice planthopper (*Nilaparvata lugens*), whitebacked rice planthopper (*Sogatella furcifera*), citrus psylla (*Diaphorina citri*), citrus whitefly (*Dialeurodes citri*), sweetpotato whitefly (*Bemisia tabaci*), greenhouse whitefly (*Trialeurodes vaporariorum*), cabbage aphid (*Brevicoryne brassicae*), cotton aphid (*Aphis gossypii*), Grain aphid (*Rhopalosiphum padi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), rice leaf bug (*Trigonotylus coelestialium* (*Kirkaldy*)), etc.; TYLENCHIDA including coffee root-lesion nematode (*Pratylenchus coffeae*), potato cyst nematode (*Globodera rostochiensis*), root-knot nematode (*Meloidogyne* sp.), citrus nematode (*Tylenchulus semipenetrans*), *Aphelenchus* sp. (*Aphelenchus avenae*), chrysanthemum foliar (*Aphelenchoides ritzemabosi*), etc.; and THYSANOPTERA including rice thrips (*Stenchaetothrips biformis*), etc. In addition, the pest control agent has little effect on useful insects such as silkworm moth (*Bombyx mori*), hornfaced mason bee (*Osmia cornifrons*) and the like and hence can be said to be a very safe insecticide. The zoological names and the like are in accordance with Applied Zoology and Entomology Society of Japan, "List of Agricultural and Forest Injurious Animals and Insects", published in 1987.

The pest control agent of the present invention has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the pest control agent of the present invention can be exhibited by applying the agent to the nursery facility, paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed. In addition, the application of the pest control agent of the present invention may be the application for which both of "penetration and translocation" are utilized, wherein the present pest control agent is applied to the nursery soil of crops, ornamental plants or the like; the picking-in hole soil at a transplantation; the plant roots; the irrigation water; or the cultural water of a water culture; so that the compound of the present invention may be absorbed from the roots through or not through the soil.

Moreover, in recent years, IPM (integrated pest management) technology using genetically modified products (herbicide-resistant products, pest-resistant products into which an insecticidal protein-generating gene has been incorporated, disease-resistant products into which a gene generating a substance inducing resistance to disease has been incorporated, products with improved taste, products with improved keeping quality, products with improved yield, etc.), insect pheromones (communication-disturbing agents used for *Tortricidae* or *Mamestra*, etc.), or natural enemy insects, has been developed. The pest control agent of the present invention can be used in admixture with such a technique, or can be used in systematization therewith.

The pest control agent of the present invention is generally prepared into suitable formulations according to a conventional manner for preparation of agrochemicals.

That is, the substituted iminoquinazolinone derivative of general formula (II') or salt thereof of the present invention and, optionally, an adjuvant are blended with a suitable inert carrier in a proper proportion and prepared into a suitable formulation such as a suspension, emulsion, soluble concentrate, wettable powder, water-dispersible granules, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, plastic carriers such as polyethylene, polypropylene, polyvinylidene chloride and the like, chemical fertilizers (e.g. ammonium sulfate, ammonium phosphate, ammonium nitrate, urea and ammonium chloride), and compost. These carriers may be used alone or as a mixture thereof.

A material usable as the liquid carrier is selected from materials that have solubility in themselves or which are without such solubility but are capable of dispersing a compound as active ingredient with the aid of an adjuvant. The following are typical examples of the liquid carrier and can be used alone or as a mixture thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbon (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination is some cases, or need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products.

Adjuvants such as silicone oils may also be used as a defoaming agent.

Adjuvants such as 1,2-benzisothiazolin-3-one, 4-chloro-3, 5-xylenol, butyl p-hydroxybenzoate may also be added as a preservative.

Further, if necessary, functional spreading agents, synergists such as metabolic inhibitor like piperonyl butoxide, anti-freezing agents such as propylene glycol, antioxidants such as BHT, ultraviolet absorbers, and the like may also be added.

The content of the compound as active ingredient may be varied as required, and the compound as active ingredient may be used in a proportion properly chosen in the range of 0.01 to 90 parts by weight per 100 parts by weight of the pest control agent of the present invention. For example, in dusts or granules, the suitable content of the compound as active ingredient is from 0.01 to 50 parts by weight. Also in emulsion or wettable powder, the suitable content is from 0.01 to 50 parts by weight.

The pest control agent of the present invention is used to control a variety of insect pests in the following manner: it is applied to a crop on which the pests are expected to appear, or a site where appearance or growth of the pests is undesirable, as it is or after being properly diluted with or suspended in water or the like, in an amount effective for control of the pests.

The applying dosage of the pest control agent of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 are depending upon purposes.

The pest control agent of the present invention may be used in admixture with other agrohorticultural insecticides, acaricides, nematocides, fungicides, biotic pesticides or the like in order to expand both spectrum of controllable insect pest species and the period of time when effective application is possible or to reduce the dosage. Furthermore, the pest control agent of the present invention may be used in admixture with herbicides, plant growth regulators, fertilizers or the like, depending upon application situations.

As the other agrohorticultural insecticides, acaricides and nematocides, which are used for the above purpose, there can be exemplified agrohorticultural insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Ethofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, tricyclohexyltin hydroxide, sodium oleate, potassium oleate, Methoprene, Hydroprene, Binapacryl, Amitraz, Dicofol, Kersen, Chrorobenzilate, Bromopropylate, Tetradifon, Bensultap, Benzoximate, Tebufenozide, Methoxyfenozide, pyridalyl, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (Bacillus thuringiensis), Azadirachtin, Rotenone, hydroxypropyl starch, Levamisole hydrochloride, Metam-sodium, Morantel tartrate, Dazomet, Trichlamide, Pasteuria penetrans, Monacrosporium-phymatophagum, etc.

As the agrohorticultural fungicides used for the same purpose as above, there can be exemplified agrohorticultural fungicides such as sulfur, lime sulfur, copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminoctadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil, Himexazol, Etridiazol, Fluoroimide, Procymidone, Vinclozolin, Iprodione, Triadimefon, Triflumizole, Bitertanol, Ipconazole, Fluconazole, Propiconazole, Diphenoconazole, Myclobutanil, Tetraconazole, Hexaconazole, Tebuconazole, Tiadinil, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl, Fthalide, Tricyclazole, Pyroquilon, Chinomethionat, Oxolinic acid, Dithianon, Kasugamycin, Validamycin, Polyoxin, Blasticidin, Streptomycin, etc.

Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Isouron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benfuresate, Fluthiacet-methyl, Quizalofop-ethyl, Bentazone, calcium peroxide, etc. As to the above nomenclature of compounds, the common names of the compounds are described except for the matters specially mentioned.

As to the biotic pesticides, the same effect as above can be expected by using the pest control agent of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as Monacrosporium phymatophagum, Steinernema carpocapsae, Steinernema kushidai, Pasteuria penetrans, etc.; microbial pesticides utilized as fungicides, such as Trichoderma lignorum, Agrobacterium radiobactor, nonpathogenic Erwinia carotovora, Bacillus subtilis, etc.; and biotic pesticides utilized as herbicides, such as Xanthomonas campestris, etc.

In addition, the pest control agent of the present invention can be used in combination with biotic pesticides including natural enemies such as Parasitic wasp (Encarsia formosa), Parasitic wasp (Aphidius colemani), Gall-mildge (Aphidoletes aphidimyza), Parasitic wasp (Diglyphus isaea), Parasitic mite (Dacnusa sibirica), Predatory mite (Phytoseiulus persimilis), Predatory mite (Amblyseius cucumeris), Predatory bug (Orius sauteri), etc.; microbial pesticides such as Beauveria brongniartii, etc.; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, (Z)-8-dodecenyl acetate, (Z)-11-tetradecenyl acetate, (Z)-13-icosen-10-one, 14-methyl-1-octadecene, etc.

EXAMPLES

Examples of the present invention are described below but they should not be construed as limiting the scope of the invention.

Example 1

Production of 1-acetyl-3,4-dihydro-3-(3-pyridylmethylamino)-6-[1,2,2,2-tetrafluoro-1-(trifluoromethyl)ethyl]-2 (1H)-quinazolinone In a 200-ml autoclave were placed 9.25 g (20 mmol) of 1-acetyl-3,4-dihydro-3-(3-pyridylmethylideneamino)-6-[1, 2,2,2-tetrafluoro-1-(trifluoromethyl)ethyl]-2(1H)-quinazolinone, 0.21 g (0.05 mmol) of 5% palladium-carbon (containing 50% water), 1.7 mg (0.01 mmol) of potassium iodide, 0.4 g (98%, 4 mmol) of concentrated sulfuric acid and 50 ml of dimethylformamide. They were heated to 45° C. with stirring and the reaction was carried out at a hydrogen pressure of 2 kg/cm$^2$ until the hydrogen absorption rate decreased. After the reaction mixture was cooled to room temperature, the catalyst was removed by filtration. The filtrate was analyzed by high performance liquid chromatography. The result is shown in Table 1 below. In addition, the filtrate was poured into 100 ml of water and the crystals precipitated were collected by filtration. The crystals were recrystallized from toluene to obtain 8.9 g of the desired compound.

Yield: 95%.

Physical property: melting point 130-132° C.

Example 2

The production was carried out under the same conditions as in Example 1, except that a halogen-containing compound added was 3.1 mg (0.015 mmol) of iodobenzene. The filtrate was analyzed by high performance liquid chromatography. The result is shown in Table 1 below.

Example 3

The production was carried out under the same conditions as in Example 1, except that a halogen-containing compound added was 1.9 mg (0.011 mmol) of 2-iodoacetamide. The filtrate was analyzed by high performance liquid chromatography. The result is shown in Table 1 below.

Example 4

The production was carried out under the same conditions as in Example 1, except that a halogen-containing compound added was 2.5 mg (0.0069 mmol) of palladium iodide. The filtrate was analyzed by high performance liquid chromatography. The result is shown in Table 1 below.

Example 5

The production was carried out under the same conditions as in Example 1, except that a halogen-containing compound added was 2.5 mg (0.0098 mmol) of iodine. The filtrate was analyzed by high performance liquid chromatography. The result is shown in Table 1 below.

Example 6

The production was carried out under the same conditions as in Example 1, except that a halogen-containing compound added was 2.5 mg (0.0011 mmol) of N-iodosuccinimide. The filtrate was analyzed by high performance liquid chromatography. The result is shown in Table 1 below.

Example 7

The production was carried out under the same conditions as in Example 1, except that a sulfur-containing compound added was 3.0 g (38 mmol) of dimethyl sulfoxide. The filtrate was analyzed by high performance liquid chromatography. The result is shown in Table 1 below.

Example 8

The production was carried out under the same conditions as in Example 1, except for using N-methylpyrrolidone as a solvent for reaction. The filtrate was analyzed by high performance liquid chromatography. The result is shown in Table 1 below.

Example 9

The production was carried out under the same conditions as in Example 1, except that a halogen-containing compound added was 2.8 mg (0.015 mmol) of 1-iodo-2-methylpropane. The filtrate was analyzed by high performance liquid chromatography. The result is shown in Table 1 below.

Example 10

The production was carried out under the same conditions as in Example 1, except that a halogen-containing compound added was 1.9 mg (0.015 mmol) of nickel chloride. The filtrate was analyzed by high performance liquid chromatography. The result is shown in Table 1 below.

Example 11

The production was carried out under the same conditions as in Example 1, except for using acetic acid as a solvent for reaction. The filtrate was analyzed by high performance liquid chromatography. The result is shown in Table 1 below.

Example 12

The production was carried out under the same conditions as in Example 1, except that a halogen-containing compound added was 3.8 mg (0.011 mmol) of 5,5-dimethyl-1,3-diiodohydantoin. The filtrate was analyzed by high performance liquid chromatography. The result is shown in Table 1 below.

Example 13

The production was carried out under the same conditions as in Example 1, except that a halogen-containing compound added was 1.7 mg (0.011 mmol) of lithium iodide. The filtrate was analyzed by high performance liquid chromatography. The result is shown in Table 1 below.

Example 14

The production was carried out under the same conditions as in Example 1, except that a halogen-containing compound added was 0.42 mg (0.011 mmol) of lithium chloride. The filtrate was analyzed by high performance liquid chromatography. The result is shown in Table 1 below.

Example 15

The production was carried out under the same conditions as in Example 1, except for using dimethylformamide:toluene/1:1 (by volume) as a solvent for reaction. The filtrate was analyzed by high performance liquid chromatography. The result is shown in Table 1 below.

Example 16

The production was carried out under the same conditions as in Example 1, except for using dimethylformamide:methanol/1:1 (by volume) as a solvent for reaction. The filtrate was analyzed by high performance liquid chromatography. The result is shown in Table 1 below.

Example 17

The production was carried out under the same conditions as in Example 1, except for using dimethylformamide:methyl t-butyl ether/1:1 (by volume) as a solvent for reaction. The filtrate was analyzed by high performance liquid chromatography. The result is shown in Table 1 below.

Example 18

The production was carried out under the same conditions as in Example 1, except for using dimethylformamide:ethyl acetate/1:1 (by volume) as a solvent for reaction. The filtrate was analyzed by high performance liquid chromatography. The result is shown in Table 1 below.

Example 19

Production of 3,4-dihydro-3-(3-pyridylmethyl-amino)-6-[1,2,2,2-tetrafluoro-1-(trifluoromethyl)ethyl]-2(1H)-quinazolinone In a 200-ml autoclave were placed 8.40 g (20 mmol) of 3,4-dihydro-3-(3-pyridylmethylideneamino)-6-[1,2,2,2-tetrafluoro-1-(trifluoromethyl)ethyl]-2(1H)-quinazolinone, 0.21 g (0.05 mmol) of 5% palladium-carbon (containing 50% water), 1.68 mg (0.01 mmol) of potassium iodide, 0.4 g (98%, 4 mmol) of concentrated sulfuric acid and 50 ml of dimethylformamide. They were heated to 45° C. with stirring and the reaction was carried out at a hydrogen pressure of 2 kg/cm$^2$ until the hydrogen absorption rate decreased. After the reaction mixture was cooled to room temperature, the catalyst was removed by filtration. The filtrate was poured into 100 ml of water and the crystals precipitated were collected by filtration. The crystals were recrystallized from toluene to obtain 8.02 g of the desired compound.

Yield: 95%.

Physical property: melting point 159-161° C.

Comparative Example 1

Production of 1-acetyl-3,4-dihydro-3-(3-pyridylmethylamino)-6-[1,2,2,2-tetrafluoro-1-(trifluoromethyl)ethyl]-2(1H)-quinazolinone (the process disclosed in JP-A-8-325239 and JP-A-2001-342186)

In a 200-ml autoclave were placed 9.25 g (20 mmol) of 1-acetyl-3,4-dihydro-3-(3-pyridylmethylideneamino)-6-[1,2,2,2-tetrafluoro-1-(trifluoromethyl)ethyl]-2(1H)-quinazolinone, 0.21 g (0.05 mmol) of 5% palladium-carbon (containing 50% water), 0.4 g (98%, 4 mmol) of concentrated sulfuric acid and 50 ml of dimethylformamide. They were heated to 60° C. with stirring and the reaction was carried out at a hydrogen pressure of 2 kg/cm$^2$ until the hydrogen absorption rate decreased. After the reaction mixture was cooled to room temperature, the catalyst was removed by filtration. The filtrate was analyzed by high performance liquid chromatography. The result is shown in Table 1 below.

Comparative Example 2

Production of 1-acetyl-3,4-dihydro-3-(3-pyridylmethylamino)-6-[1,2,2,2-tetrafluoro-1-(trifluoromethyl)ethyl]-2(1H)-quinazolinone (the process described in J. Org. Chem., 26, 1854 (1961))

In a 200-ml autoclave were placed 9.25 g (20 mmol) of 1-acetyl-3,4-dihydro-3-(3-pyridylmethylideneamino)-6-[1,2,2,2-tetrafluoro-1-(trifluoromethyl)ethyl]-2(1H)-quinazolinone, 12.4 mg (0.055 mmol) of platinum oxide and 50 ml of dimethylformamide. They were heated to 60° C. with stirring and the reaction was carried out at a hydrogen pressure of 2 kg/cm$^2$ until the hydrogen absorption rate decreased. After the reaction mixture was cooled to room temperature, the catalyst was removed by filtration. The filtrate was analyzed by high performance liquid chromatography. The result is shown in Table 1 below.

In Table 1, the term "starting material" means 1-acetyl-3,4-dihydro-3-(3-pyridylmethylideneamino)-6-[1,2,2,2-tetrafluoro-1-(trifluoromethyl)ethyl]-2(1H)-quinazolinone, the term "desired compound" means 1-acetyl-3,4-dihydro-3-(3-pyridylmethylamino)-6-[1,2,2,2-tetrafluoro-1-(trifluoromethyl)ethyl]-2(1H)-quinazolinone, the term "by-product 1" means 3,4-dihydro-3-(3-pyridylmethyl-amino)-6-[1,2,2,2-tetrafluoro-1-(trifluoromethyl)ethyl]-2(1H)-quinazolinone, the term "by-product 2" means 1-acetyl-3,4-dihydro-3-amino-6-[1,2,2,2-tetrafluoro-1-(trifluoromethyl)ethyl]-2(1H)-quinazolinone, and the term "by-product 3" means 1-acetyl-3,4-dihydro-6-[1,2,2,2-tetrafluoro-1-(trifluoromethyl)ethyl]-2(1H)-quinazolinone.

[Table 1]

TABLE 1

| | Area percentage of components (%) | | | | |
|---|---|---|---|---|---|
| | Starting material | Desired compound | By-product 1 | By-product 2 | By product 3 |
| Example 1 | 0 | 98 | 0 | 0.6 | 0.7 |
| Example 2 | 0 | 98 | 0 | 1 | 1 |
| Example 3 | 0 | 98 | 0 | 0.9 | 0.7 |
| Example 4 | 0 | 99 | 0 | 0.4 | 0.6 |
| Example 5 | 0 | 96 | 0 | 2 | 1.5 |
| Example 6 | 0 | 97 | 0 | 0.9 | 1 |
| Example 7 | 0 | 96 | 0 | 1.9 | 1.4 |
| Example 8 | 0 | 97 | 0 | 0.8 | 1.2 |
| Example 9 | 0 | 98 | 0 | 0.7 | 0.9 |
| Example 10 | 0 | 95 | 0 | 2 | 1.9 |
| Example 11 | 2 | 95 | 0 | 2 | 2 |
| Example 12 | 0 | 94 | 0.2 | 1.1 | 1.8 |
| Example 13 | 0 | 97 | 0.1 | 0.9 | 1.8 |
| Example 14 | 0 | 94 | 0.8 | 1.5 | 3.5 |
| Example 15 | 0 | 96 | 0.2 | 1.0 | 1.7 |
| Example 16 | 0 | 95 | 0.8 | 1.9 | 1.2 |
| Example 17 | 0 | 98 | 0.2 | 1.0 | 0.7 |
| Example 18 | 0 | 97 | 0.7 | 1.1 | 1.0 |
| Comparative Example 1 | 2 | 85 | 1 | 6 | 6 |
| Comparative Example 2 | 50 | 22 | 5 | 2 | 21 |

From these examples and the results shown in Table 1, it can be seen that the production process of the present invention reduces the amounts of the by-products and greatly improves the selectivity and yield of the desired compound as compared with the comparable examples.

Production examples of intermediates represented by general formula (II') are described below.

Production Example 1

Production of 1-methyl-3-(3-pyridylmethylideneamino)-3,4-dihydro-6-[1,2,2,2-tetrafluoro-1-(trifluoromethyl)ethyl]-2(1H)-quinazolinone (compound No. 1)

In 10 ml of dimethylformamide was dissolved 0.84 g (2.0 mmol) of 3-(3-pyridylmethylideneamino)-3,4-dihydro-6-[1,2,2,2-tetrafluoro-1-(trifluoromethyl)ethyl]-2(1H)-quinazolinone, and to the resulting solution was added 0.09 g (2.3 mmol) of sodium hydride (purity: 62.4%). The reaction was carried out at room temperature for 30 minutes, after which 0.34 g (2.4 mmol) of methyl iodide was added and the reaction was carried out for 4 hours. After completion of the reaction, the reaction solution was poured into ice water and the desired compound was extracted with ethyl acetate (20 ml×3). The extract solution was washed with water and saturated aqueous sodium chloride solution, dried over anhydrous magnesium sulfate, and then concentrated in vacuo. The crude product thus obtained was purified by silica gel column chromatography (ethyl acetate–methanol=10:1) to obtain 0.44 g of the desired compound.

Physical property: melting point>300° C.
Yield: 50.7%.

Production Example 2

Production of 1-acetyl-3-(3-pyridylmethylideneamino)-3,4-dihydro-6-[1,2,2,2-tetrafluoro-1-(trifluoromethyl)ethyl]-2(1H)-quinazolinone (compound No. 8)

In 10 ml of dimethylformamide was dissolved 0.84 g (2.0 mmol) of 3-(3-pyridylmethylideneamino)-3,4-dihydro-6-[1,2,2,2-tetrafluoro-1-(trifluoromethyl)ethyl]-2(1H)-quinazolinone, and to the resulting solution was added 0.09 g (2.3 mmol) of sodium hydride (purity: 62.4%). The reaction was carried out at room temperature for 30 minutes, after which 0.19 g (2.4 mmol) of acetyl chloride was added and the reaction was carried out for 4 hours. After completion of the reaction, the reaction solution was poured into ice water and the desired compound was extracted with ethyl acetate (20 ml×3). The extract solution was washed with water and saturated aqueous sodium chloride solution, dried over anhydrous magnesium sulfate, and then concentrated in vacuo. The crude product thus obtained was purified by silica gel column chromatography (ethyl acetate–methanol 10:1) to obtain 0.51 g of the desired compound.

Physical property: melting point 160-162° C.
Yield: 55.1%.

Production Example 3

Production of 1-acetyl-3-(3-pyridylmethylideneamino)-3,4-dihydro-6-[1,2,2,2-tetrafluoro-1-(trifluoromethyl)ethyl]-2(1H)-quinazolinone (compound No. 8)

In 10 ml of dimethylacetamide was dissolved 0.84 g (1.8 mmol) of 3-(3-pyridylmethylideneamino)-3,4-dihydro-6-[1,2,2,2-tetrafluoro-1-(trifluoromethyl)ethyl]-2(1H)-quinazolinone, and to the resulting solution was added 0.09 g (2.3 mmol) of sodium hydride (purity: 62.4%). The reaction was carried out at room temperature for 30 minutes, after which 0.25 g (2.4 mmol) of acetic anhydride was added and the reaction was carried out for 4 hours. After completion of the reaction, the reaction solution was poured into ice water and the desired compound was extracted with ethyl acetate (20 ml×3). The extract solution was washed with water and saturated aqueous sodium chloride solution, dried over anhydrous magnesium sulfate, and then concentrated in vacuo. The crude product thus obtained was purified by silica gel column chromatography (ethyl acetate–methanol=10:1) to obtain 0.78 g of the desired compound.

Physical property: melting point 160-162° C.
Yield: 92.5%.

Typical compounds as the substituted imino-quinazolinone derivative of general formula (II'), which can be produced in the same manner as in the above production examples, are listed below in Table 2 to Table 4, but they are not intended in any way to limit the scope of the present invention. In the following tables, "n-" is a prefix for "normal", "i-" is a prefix for "iso", "s-" is a prefix for "secondary", "c-" is a prefix for "cyclo", and "Ph" indicates a phenyl group and "Naphthyl" a naphthyl group.

General Formula (II'-2)

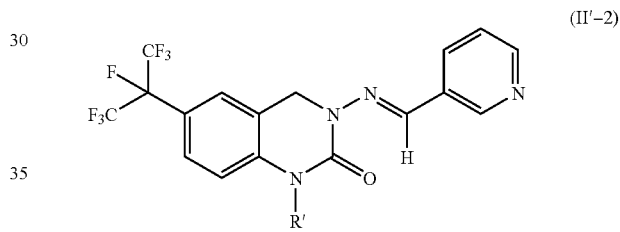

[Table 2]

TABLE 2

| No. | R' | Melting point (° C.) or nD(° C.) |
|---|---|---|
| 1 | CH$_3$ | >300 |
| 2 | C$_2$H$_5$ | |
| 3 | C$_3$H$_7$-n | |
| 4 | CH$_2$OCH$_3$ | 95-98 |
| 5 | CH$_2$OC$_2$H$_5$ | 116-120 |
| 6 | CH$_2$CN | 220-223 |
| 7 | CHO | >300 |
| 8 | COCH$_3$ | 160-162 |
| 9 | COC$_2$H$_5$ | 120-122 |
| 10 | COC$_3$H$_7$-n | 110-112 |
| 11 | COC$_3$H$_7$-i | 199-201 |
| 12 | COC$_4$H$_9$-n | 1.5876(23) |
| 13 | COC$_4$H$_9$-s | |
| 14 | COC$_3$H$_5$-c | 141-143 |
| 15 | COCH$_2$OCH$_3$ | 106-109 |
| 16 | COOCH$_3$ | 125-130 |
| 17 | COOC$_2$H$_5$ | 162-163 |
| 18 | COOC$_3$H$_7$-n | 166-168 |
| 19 | COOC$_3$H$_7$-i | 158-160 |
| 20 | COOC$_4$H$_9$-n | 163-166 |
| 21 | COOC$_4$H$_9$-s | |
| 22 | SO$_2$CH$_3$ | 144-147 |
| 23 | SO$_2$C$_2$H$_5$ | |
| 24 | COPh | 171-173 |
| 25 | COPh-2-CF$_3$ | 184-188 |
| 26 | COPh-3-CF$_3$ | 175-177 |
| 27 | COPh-4-CF$_3$ | 144-145 |

TABLE 2-continued

| No. | R' | Melting point (° C.) or nD(° C.) |
|---|---|---|
| 28 | COPh-4-F | 152-157 |
| 29 | COPh-2-OCH$_3$ | 180-181 |
| 30 | COPh-3-CH$_3$ | 142-143 |
| 31 | COPh-3,4-Cl$_2$ | 137-140 |
| 32 | COPh-4-Ph | 52-58 |
| 33 | CONaphthyl-1 | 100-104 |

General Formula (II'-3)

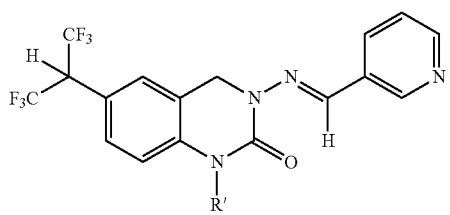

(II'-3)

[Table 3]

TABLE 3

| No. | R' | Melting point (° C.) or nD(° C.) |
|---|---|---|
| 34 | CH$_3$ | |
| 35 | C$_2$H$_5$ | |
| 36 | C$_3$H$_7$-n | |
| 37 | CH$_2$OCH$_3$ | |
| 38 | CH$_2$OC$_2$H$_5$ | |
| 39 | CH$_2$CN | |
| 40 | CHO | |
| 41 | COCH$_3$ | |
| 42 | COC$_2$H$_5$ | |
| 43 | COC$_3$H$_7$-n | |
| 44 | COC$_3$H$_7$-i | |
| 45 | COC$_4$H$_9$-n | |
| 46 | COC$_4$H$_9$-s | |
| 47 | COC$_3$H$_5$-c | |
| 48 | COCH$_2$OCH$_3$ | |
| 49 | COOCH$_3$ | |
| 50 | COOC$_2$H$_5$ | |
| 51 | COOC$_3$H$_7$-n | |
| 52 | COOC$_3$H$_7$-i | |
| 53 | COOC$_4$H$_9$-n | |
| 54 | COOC$_4$H$_9$-s | |
| 55 | SO$_2$CH$_3$ | |
| 56 | SO$_2$C$_2$H$_5$ | |
| 57 | COPh | |
| 58 | COPh-2-CF$_3$ | |
| 59 | COPh-3-CF$_3$ | |
| 60 | COPh-4-CF$_3$ | |
| 61 | COPh-4-F | |
| 62 | COPh-2-OCH$_3$ | |
| 63 | COPh-3-CH$_3$ | |
| 64 | COPh-3,4-Cl$_2$ | |
| 65 | COPh-4-Ph | |
| 66 | CONaphthyl-1 | |

General Formula (II'-4)

(II'-4)

[Table 4]

TABLE 4

| No. | R' | Melting point (° C.) or nD(° C.) |
|---|---|---|
| 67 | CH$_3$ | |
| 68 | C$_2$H$_5$ | |
| 69 | C$_3$H$_7$-n | |
| 70 | CH$_2$OCH$_3$ | |
| 71 | CH$_2$OC$_2$H$_5$ | |
| 72 | CH$_2$CN | |
| 73 | CHO | |
| 74 | COCH$_3$ | |
| 75 | COC$_2$H$_5$ | |
| 76 | COC$_3$H$_7$-n | |
| 77 | COC$_3$H$_7$-i | |
| 78 | COC$_4$H$_9$-n | |
| 79 | COC$_4$H$_9$-s | |
| 80 | COC$_3$H$_5$-c | |
| 81 | COCH$_2$OCH$_3$ | |
| 82 | COOCH$_3$ | |
| 83 | COOC$_2$H$_5$ | |
| 84 | COOC$_3$H$_7$-n | |
| 85 | COOC$_3$H$_7$-i | |
| 86 | COOC$_4$H$_9$-n | |
| 87 | COOC$_4$H$_9$-s | |
| 88 | SO$_2$CH$_3$ | |
| 89 | SO$_2$C$_2$H$_5$ | |
| 90 | COPh | |
| 91 | COPh-2-CF$_3$ | |
| 92 | COPh-3-CF$_3$ | |
| 93 | COPh-4-CF$_3$ | |
| 94 | COPh-4-F | |
| 95 | COPh-2-OCH$_3$ | |
| 96 | COPh-3-CH$_3$ | |
| 97 | COPh-3,4-Cl$_2$ | |
| 98 | COPh-4-Ph | |
| 99 | CONaphthyl-1 | |

Typical formulation examples and test examples of the present invention are described below but they should not be construed as limiting the scope of the invention.

As used in the formulation examples, the terms "part" and "parts" are by weight. As comparative compounds, there were used 1-acetyl-3-(3-pyridylmethylideneamino)-3,4-dihydro-2(1H)-quinazolinone (compound No. 381 disclosed in JP-A-8-325239, hereinafter referred to as compound A) and 1-acetyl-3-(3-pyridylmethylamino)-3,4-dihydro-6-bromo-2(1H)-quinazolinone (compound No. 334 disclosed in JP-A-2001-342186, hereinafter referred to as compound B).

| Formulation Example 1 | |
|---|---|
| Each compound listed in Tables 2 to 4 or each comparative compound | 10 parts |
| Xylene | 70 parts |
| N-methylpyrrolidone | 10 parts |
| Mixture of polyoxyethylene nonylphenyl ether and calcium alkylbenzenesulfonate | 10 parts |

-continued

Formulation Example 1

An emulsion was prepared by mixing uniformly the above ingredients to effect dissolution.

Formulation Example 2

| | |
|---|---|
| Each compound listed in Tables 2 to 4 or each comparative compound | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 2 to 4 or each comparative compound | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 2 to 4 or each comparative compound | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal Effect on Green Peach Aphid (*Myzus persicae*)

A Chinese cabbage plant was planted in each of plastic pots with a diameter of 8 cm and a height of 8 cm, and green peach aphids were propagated on the plant, after which the parasites in each pot were counted. A preparation containing each compound of the present invention listed in Tables 2 to 4 or each comparative compound as an active ingredient was dispersed in and diluted with water to obtain a 500 ppm liquid chemical. The stalks and leaves of the potted Chinese cabbage plants were sprayed with the liquid chemical and air-dried, and then the pots were stored in a greenhouse. Six days after the spraying, green peach aphids parasitic on each Chinese cabbage plant were counted and the control efficacy was calculated by the following equation, whereby the insecticidal effect was judged according to the criterion shown below. The result is shown in Table 5 below.

Control efficacy=$100-\{(T \times Ca)/(Ta \times C)\} \times 100$

Ta: number of parasites before spraying in treated group,
T: number of parasites after spraying in treated group,
Ca: number of parasites before spraying in untreated group,
C: number of parasites after spraying in untreated group.

Criterion for judgment:

| | | |
|---|---|---|
| A | Control efficacy | 100% |
| B | Control efficacy | 99-90% |
| C | Control efficacy | 89-80% |
| D | Control efficacy | 79-50% |

Test Example 2

Insecticidal Effect on Greenhouse Whitefly (*Trialeuroddes vaporariorum*)

A preparation containing each compound of the present invention listed in Tables 2 to 4 or each comparative compound as an active ingredient was dispersed in and diluted with water to obtain a 100 ppm liquid chemical. A tomato leaf set in a 20-ml vial with its stalk immersed in water was sprayed with the liquid chemical with a spray gun on a turntable. After air-dryness, the treated leaf was placed in a glass cylinder and inoculated with 20 adult greenhouse whiteflies. After the treatment, the glass cylinder was placed in a greenhouse. Four days after the inoculation, the living insects were counted. The corrected mortality was calculated according to the following equation and the insecticidal effect was judged according to the criterion shown below. The result is shown in Table 5 below.

$$\text{Corrected mortality (\%)} = \frac{\text{Number of living insects in untreated group} - \text{Number of living insects in treated group}}{\text{Number of living insects in untreated group}} \times 100$$

Criterion for Judgment:

| | | |
|---|---|---|
| A | Corrected mortality | 100% |
| B | Corrected mortality | 99-90% |
| C | Corrected mortality | 89-80% |
| D | Corrected mortality | 79-50% |

Test Example 3

Insecticidal Effect on White Peach Scale (*Pseudaulacaspis pentagona*)

A preparation containing each compound of the present invention listed in Tables 2 to 4 or each comparative compound as an active ingredient was dispersed in and diluted with water to obtain a 100 ppm liquid chemical. A potato tuber with first-instar larvae of white peach scale as parasites was sprayed with the liquid chemical with a spray gun. Fourteen days after the treatment, the living insects were counted. In the same manner as in Test Example 2, the corrected mortality was calculated and the insecticidal effect was judged. The result is shown in Table 5 below.

[Table 5]

TABLE 5

| No. | Test Example 1 | Test Example 2 | Test Example 3 |
|---|---|---|---|
| 1 | A | A | A |
| 2 | A | A | A |
| 3 | A | A | A |
| 4 | A | A | A |
| 5 | A | A | A |
| 6 | A | A | A |
| 7 | A | A | A |
| 8 | A | A | A |
| 9 | A | A | A |
| 10 | A | A | A |
| 11 | A | A | A |
| 12 | A | A | A |
| 13 | A | A | A |
| 14 | A | A | A |
| 15 | A | A | A |
| 16 | A | A | A |
| 17 | A | A | A |
| 18 | A | A | A |
| 19 | A | A | A |
| 20 | A | A | A |
| 21 | A | A | A |
| 22 | A | A | A |
| 23 | A | A | A |
| 24 | A | A | A |
| 25 | A | A | A |
| 26 | A | A | A |
| 27 | A | A | A |
| 28 | A | A | A |
| 29 | A | A | A |
| 30 | A | A | A |
| 31 | A | A | A |
| 32 | A | A | A |
| 33 | A | A | A |
| Comparative compound A | A | A | B |
| Comparative compound B | A | C | C |

Test Example 4

Insecticidal Effect on Greenhouse (*Trialeuroddes vaporariorum*) at a Low Dosage The same test as in Test Example 2 was carried out except for changing the concentration of the liquid chemical to 3 ppm. As a result, it was found that compounds Nos. 8 to 12 and 14 to 20 of the present invention exhibited marked controlling effect rated A, while comparative compound A exhibited controlling effect rated C and comparative compound B exhibited controlling effect rated D.

Test Example 5

Insecticidal Effect on White Peach Scale (*Pseudaulacaspis pentagona*) at a Low Dosage The same test as in Test Example 3 was carried out except for changing the concentration of the liquid chemical to 30 ppm. As a result, it was found that compounds Nos. 8 to 12 and 14 to 20 of the present invention exhibited marked controlling effect rated A, while comparative compound A and comparative compound B exhibited controlling effect rated D.

The invention claimed is:

1. A process for producing a substituted aminoquinazolinone represented by formula (I):

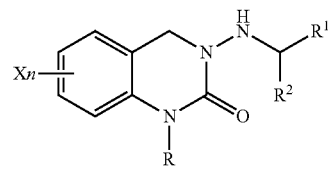

(wherein R, $R^1$, $R^2$, X and n are as defined below), which comprises reducing a substituted iminoquinazolinone represented by formula (II):

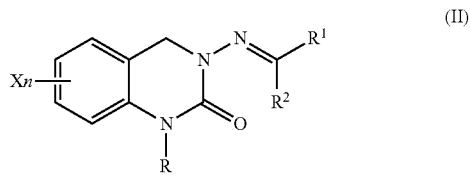

(wherein R is a hydrogen atom; a formyl group; a ($C_1$-$C_6$) alkyl group; a ($C_1$-$C_6$)alkoxy($C_1$-$C_3$)alkyl group; a ($C_1$-$C_6$) alkylsulfonyl group; a cyano($C_1$-$C_3$)alkyl group; a ($C_1$-$C_6$) alkylcarbonyl group; a ($C_1$-$C_6$)alkoxycarbonyl group; a ($C_1$-$C_3$)alkoxy($C_1$-$C_6$)alkylcarbonyl group; a ($C_3$-$C_6$) cycloalkylcarbonyl group; a phenylcarbonyl group; a substituted phenylcarbonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$)alkoxy group, a halo($C_1$-$C_6$)alkoxy group, a ($C_1$-$C_6$) alkylthio group, a halo($C_1$-$C_6$)alkylthio group and a phenyl group; a phenylsulfonyl group; a substituted phenylsulfonyl group having 1 to 5 substituents which may be the same or different and are selected from the group consisting of a halogen atom, a nitro group, a cyano group, a ($C_1$-$C_6$)alkyl group, a halo($C_1$-$C_6$)alkyl group, a ($C_1$-$C_6$)alkoxy group, a halo($C_1$-$C_6$)alkoxy group, a ($C_1$-$C_6$)alkylthio group and a halo($C_1$-$C_6$)alkylthio group; or a naphthylcarbonyl group, $R^1$ is a 5- or 6-membered heterocyclic group having 1 to 3 heteroatoms which may be the same or different and are selected from the group consisting of oxygen atom, sulfur atom and nitrogen atom, said heterocyclic group being able to have 1 to 5 substituents which may be the same or different and are selected from the group consisting of a halogen atom, a cyano group, a ($C_1$-$C_6$)alkyl group, a halo($C_1$-$C_6$)alkyl group and a ($C_1$-$C_6$)alkoxy groups, and a nitrogen atom in the heterocyclic group being able to represent an N-oxide group, $R^2$ is a hydrogen atom or a ($C_1$-$C_3$)alkyl group, each of Xs, which may be the same or different, is a halogen atom, a ($C_1$-$C_6$)alkyl group, a halo($C_1$-$C_6$)alkyl group, a ($C_1$-$C_6$)alkoxy group, a halo($C_1$-$C_6$)alkoxy group or a pentafluorosulfanyl group, and n is an integer of 0 to 4) with hydrogen in the presence of a catalyst and an additive, wherein the catalyst is a palladium-based catalyst; the additive is iodine, iodobenzene, 2-iodoacetamide, N-iodosuccinimide, 5,5-dimethyl-1,3-diiodohydantoin, palladium iodide, 1-iodo-2-methylpropane, lithium iodide, sodium iodide, potassium iodide, dimethyl sulfoxide or diphenyl sulfoxide.

2. A process for producing a substituted aminoquinazolinone according to claim 1, wherein R is a hydrogen atom, a ($C_1$-$C_6$)alkyl group, a ($C_1$-$C_6$)alkylcarbonyl group, a ($C_1$-$C_6$) alkoxycarbonyl group, a ($C_1$-$C_3$)alkoxy($C_1$-$C_6$)alkylcarbonyl group or a ($C_3$-$C_6$)cycloalkylcarbonyl group; $R^1$ is a pyridyl group; $R^2$ is a hydrogen atom; each of Xs, which may be the same or different, is a halogen atom, a ($C_1$-$C_6$)alkyl group, a halo($C_1$-$C_6$)alkyl group, a ($C_1$-$C_6$)alkoxy group, a halo($C_1$-$C_6$)alkoxy group or a pentafluorosulfanyl group; and n is an integer of 0 to 2.

3. A process for producing a substituted aminoquinazolinone according to claim 1, wherein R is a hydrogen atom or a ($C_1$-$C_6$)alkylcarbonyl group; $R^1$ is a 3-pyridyl group; $R^2$ is a hydrogen atom; each of Xs is a halo($C_1$-$C_6$)alkyl group or a pentafluorosulfanyl group; and n is 1.

* * * * *